(12) United States Patent
Hsu et al.

(10) Patent No.: US 6,420,333 B1
(45) Date of Patent: Jul. 16, 2002

(54) MANUFACTURE OF CAPSULES FOR INCORPORATION INTO DETERGENT AND PERSONAL CARE COMPOSITIONS

(75) Inventors: Feng-Lung Gordon Hsu, Tenafly; Kristina Marie Neuser, Cliffside Park; MyongSuk Bae-Lee, Montville, all of NJ (US); Eric Charles Ehrnsperger, Chestnut Ridge, NY (US); Tracy Bowens, East Orange, NJ (US)

(73) Assignee: Unilever Home & Personal Care USA division of Conopco, Inc., Greenwich, CT (US)

( * ) Notice: Subject to any disclaimer, the term of this patent is extended or adjusted under 35 U.S.C. 154(b) by 0 days.

(21) Appl. No.: 09/940,740

(22) Filed: Aug. 28, 2001

(51) Int. Cl.[7] .......................... C11D 3/386; C11D 17/08
(52) U.S. Cl. .................... 510/441; 510/130; 510/208; 510/213; 510/226; 510/276; 510/300; 510/305; 510/342; 510/356; 510/421; 510/432; 510/438; 510/392; 510/442; 510/530
(58) Field of Search ................. 510/441, 130, 510/208, 213, 226, 276, 300, 305, 342, 356, 421, 432, 438, 392, 442, 530

(56) References Cited

U.S. PATENT DOCUMENTS

| | | | | |
|---|---|---|---|---|
| 4,090,973 A | * | 5/1978 | Maguire, Jr. et al. | 252/89 R |
| 4,801,544 A | * | 1/1989 | Munk | 435/188 |
| 4,898,781 A | * | 2/1990 | Onouchi et al. | 428/402.22 |
| 4,906,396 A | | 3/1990 | Falholt et al. | 252/174.12 |
| 5,281,356 A | * | 1/1994 | Tsaur et al. | 252/174.13 |
| 5,296,166 A | | 3/1994 | Leong | 252/314 |
| 5,354,669 A | | 10/1994 | Kaluza et al. | 435/91.53 |
| 5,434,069 A | * | 7/1995 | Tsaur et al. | 435/188 |
| 5,441,660 A | | 8/1995 | Tsaur et al. | 252/95 |
| 5,589,370 A | * | 12/1996 | Ratuiste et al. | 264/4.3 |
| 5,733,531 A | | 3/1998 | Mitchnick | 424/59 |
| 5,879,694 A | | 3/1999 | Morrison et al. | 424/405 |

FOREIGN PATENT DOCUMENTS

| | | |
|---|---|---|
| EP | 0 273 775 | 7/1988 |
| GB | 2 186 884 | 8/1987 |
| WO | 91/01366 | 2/1991 |
| WO | 01/05949 | 1/2001 |

OTHER PUBLICATIONS

Derwent Abstract of SU 1 311 253—published Mar. 10, 1995.

Abstract of JP 41 003 667 6A—published Feb. 10, 1998.

* cited by examiner

*Primary Examiner*—Charles Boyer
(74) *Attorney, Agent, or Firm*—Rimma Mitelman

(57) ABSTRACT

A process for encapsulating a benefit agent and/or colorant for personal care or detergent compositions, the process comprising immersing an emulsion or a dispersion containing the benefit agent and/or colorant into an aqueous curing solution containing a high HLB surfactant and/or a superwetting agent. The preferred process further includes increasing the density of the droplets, to allow for easier penetration into the curing solution.

13 Claims, No Drawings

MANUFACTURE OF CAPSULES FOR INCORPORATION INTO DETERGENT AND PERSONAL CARE COMPOSITIONS

FIELD OF THE INVENTION

A process of encapsulating a variety of ingredients, the process resulting in capsules suitable for incorporation into detergent or personal care compositions.

BACKGROUND OF THE INVENTION

In many articles of commerce, particularly consumer products, it is desirable to separate certain ingredients, yet have them disposed in a common container. Separation is particularly beneficial where one or more ingredients have negative interactions with each other. For example, in laundry detergents, enzymes are useful in removing stains but it is also best to separate them from other constituents, such as sources of alkalinity and surfactants, especially anionic surfactants like linear alkylbenzene sulfonates or alkyl sulfates. Bleaches, vitamins, perfumes, vegetable oils, plant extracts and ceramides are further examples of ingredients that sometimes need to be separated from the rest of the detergent or personal care composition.

A known technique for separating ingredients in a common container includes encapsulation. Encapsulation technology is well known for different applications. Generally, encapsulation includes a medium that surrounds at least one component and thereby provides a barrier between the "encapsulated" component and other components. The barrier is typically temporary and is designed to break down and release the encapsulated material at a desired time, such as at a particular temperature, upon reaction or dissolution with chemicals, or due to mechanical stress. Methods of encapsulation include coacervation, liposome formation, granulation, coating, emulsification, atomization and spray-cooling.

See, for instance, the disclosures of enzyme encapsulates and encapsulation processes: Falholt et al. (U.S. Pat. No. 4,906,396, UK 2,186 884, and EP 0 273 775), Tsaur et al. (U.S. Pat. Nos. 5,434,069 and 5,441,660), Ratuiste et al. (U.S. Pat. No. 5,589,370). JP 41003667 discloses a dialysis of a protein solution against polyol-base polymer. WO 01/05949 discloses a method for densifying enzyme capsules. See also Mitchnik et al. (U.S. Pat. No. 5,733,531) and Leong (U.S. Pat. No. 5,296,166).

Some of the prior art techniques have particular drawbacks. For example, atomization methods can require special air handling techniques (to avoid respiratory risks). Capsule geometry (size/shape) can also be hard to control. An additional particular problem is to prevent capsule agglomeration after formation—known capsules frequently agglomerate due to tacky hydrophobic encapsulating materials at the capsule surface.

An additional challenge exists when capsules, e.g., enzyme capsules have a lower density than a liquid composition for which they are intended, especially liquid detergent composition. In this case, the density of the enzyme capsule is less than one as a result of the density of the hydrophobe (typical encapsulating material) ranging from 0.8 to 0.9 g/L. Since most liquid detergents have a density of slightly greater than 1, and the density of the enzyme capsule is less than 1, the enzyme capsules will float and form a layer on the top portion of the liquid formulation. Such formulation is unfavorable because a uniform distribution of the capsules is required for the formulation to be delivered consistently, as well as the appearance of the formulation is undesirable. In addition, capsule concentration at the surface of the composition is conducive to further agglomeration.

Consequently, reliable, efficient and cost effective methods of manufacturing encapsulated products are desirable.

SUMMARY OF THE INVENTION

The present invention includes a process for forming encapsulated benefit agent and/or colorant for personal care or detergent compositions, the process comprising immersing droplets of an emulsion or a dispersion containing a hydrophobic material and the benefit agent and/or colorant into an aqueous curing solution, the aqueous curing solution containing a high HLB surfactant and/or a super-wetting agent.

The following detailed description and the examples illustrate some of the effects of the inventive compositions. The invention and the claims, however, are not limited to the following description and examples.

DETAILED DESCRIPTION OF THE INVENTION

Except in the operating and comparative examples, or where otherwise explicitly indicated, all numbers in this description indicating amounts of material or conditions of reaction, physical properties of materials and/or use are to be understood as modified by the word "about." All amounts are by weight, unless otherwise specified.

For the avoidance of doubt the word "comprising" is intended to mean "including" but not necessarily "consisting of" or "composed of." In other words the listed steps or options need not be exhaustive.

The term "continuous" does not necessarily mean "isotropic". The term "continuous" is used herein to denote the phase which is predominant in volume during emulsification or dispersion of discontinuous phase in the continuous phase.

The term "hydrocarbon oil" as used herein means a hydrocarbon oil having a maximum viscosity of about 10 kg/(m)(sec), preferably no greater than about 5 kg/(m)(sec).

The term "wax" as used herein means a hydrophobic material which is a solid at 20° C. By "solid" is meant the ingredient is not mobile at 20° C.

The following describes two preferred methods of making encapsulated particles wherein a continuous phase (for convenience, sometimes hereinafter called "shell") encapsulates or surrounds a discontinuous phase containing the desired ingredient.

Shell

The shell material is preferably a hydrophobic material such as, for example, paraffin, oil, wax or petroleum jelly ("petrolatum"), a polymer, and mixtures thereof. However, it is within the scope of the present disclosure that other suitable materials can be used as the shell material.

In one preferred embodiment of the invention, a mixture of a thermoplastic block co-polymer and a hydrocarbon oil is employed, particularly when it is desired to make transparent capsules. The block co-polymers particularly suitable in the present invention are block co-polymers containing at least one rigid block and at least one flexible block. The mixture of the hydrocarbon oil and the block co-polymer according to the present invention is isotropic at 20° C. It should be understood that since the co-polymer is not pourable at 20° C. (indeed, it is solid), it may be difficult to combine the co-polymer with the oil at such temperature to ascertain whether the mixture is isotropic. According to the present invention, a mixture may be formed at any suitable temperature at which the liquefied co-polymer forms an isotropic liquid mixture with the oil. The copolymer/oil mixtures suitable for use in the present invention, however, remain isotropic after cooling. Suitable isotropic mixtures have transmittance of at least 50% preferably at least 70%, as measured by UV-visible spectrophotometer (measured in visible light range).

In one embodiment of the invention, the co-polymer employed in the continuous phase of the capsules is selected from the group consisting of a triblock co-polymer, radial co-polymer, and multiblock co-polymer, the co-polymer comprising at least one triblock with a structure: rigid block—flexible block—rigid block. Preferably the rigid block is styrene-type polymer, and the flexible block is rubber-type polymer. By virtue of employing the rigid-flexible-rigid block co-polymer, the viscosity of the oil is increased, and the hardened continuous phase is formed, yet the resulting capsule is sufficiently soft and friable to release the discontinuous phase in normal use. The co-polymer blends uniformly with oil at a temperature which is much lower than the melting point of wax, thus allowing for encapsulation of temperature-sensitive ingredients, e.g. bleach, perfume, enzyme, vegetable oil, etc. A further advantage of using the co-polymer is that it is not necessary (although possible) to use a surfactant in preparing a uniform distribution of the discontinuous phase in the continuous phase; the avoidance of the surfactant makes the encapsulation process easier and cheaper. Furthermore, the absence of surfactant improves the stability of the encapsulated ingredient, since the surfactant provides for a potential channel of penetration for an external environment.

The preferred co-polymers are transparent and uncolored, in order to attain a transparent and uncolored continuous phase.

Examples of suitable co-polymers include but are not limited to those that are described in Morrison et al. (U.S. Pat. No. 5,879,694) hereby incorporated by reference herein.

Each of the triblock, radial block and/or multiblock copolymers in the invention contains at least two thermodynamically incompatible segments. By the expression thermodynamically incompatible with respect to the polymers, it is meant that the polymer contains at least two incompatible segments, for example at least one hard and one soft segment. In general, in a triblock polymer, the ratio of segments is one hard, one soft, one hard or an A-B-A copolymer. The multiblock and radial block copolymers can contain any combination of hard and soft segments, provided that there are both hard and soft characteristics. In the optional diblock copolymer, the blocks are sequential with respect to hard and soft segments.

Commercially available thermoplastic rubber type polymers which are especially useful in forming the compositions of the present invention are sold under the trademark Kraton® by Shell Chemical Company. The Kraton® rubber polymers are described as elastomers which have an unusual combination of high strength and low viscosity and a unique molecular structure of linear diblock, triblock and radial copolymers. Each molecule of the Kraton® rubber is said to consist of block segments of styrene monomer units and rubber monomer and/or comonomer units. Each block segment may consist of 100 or more monomer or comonomer units. The most common structure is the linear ABA block type; styrene-butadiene-styrene (SBS) and styrene-isoprene-styrene (SIS), which is the Kraton® D rubber series.

A second generation polymer of this general type is the Kraton® G series. This copolymer comprises a styrene-ethylene-butylene-styrene type (S-EB-S) structure. The Kraton® G series is preferred in the practice of the invention, as the copolymers of this series are hydrogenated and thus more thermally stable; that is, decomposition is less likely to occur during blending of the G series polymers with the oil (the D series polymers having unsaturation within the rubber block). The Kraton® G rubbers are indicated as being compatible with paraffinic and naphthenic oils and the triblock copolymers are reported as taking up more than 20 times their weight in oil to make a product which can vary in consistency from a "Jello®" to a strong elastic rubbery material depending on the grade and concentration of the rubber. The optionally blended diblock polymers include the AB type such as styrene-ethylenepropylene (S-EP) and styrene-ethylenebutylene (S-EB), styrene-butadiene (SB) and styrene-isoprene (SI).

Preferably, when Kraton® series block co-polymers are employed (i.e., styrene-elastomer block co-polymers), the oil is essentially free of silicone-containing oils, in order to obtain optimum isotropic mixtures. By "essentially free" is meant that in the Kraton®/oil continuous phase, the amount of silicone-containing oil is preferably less than 2%, by weight of the continuous phase, more preferably less than 1%, most preferably less than 0.5% and optimally is 0%.

The preferred polymer is a triblock polymer of the Kraton® G type, in particular Kraton® G-1650. Kraton® G-1650 is an SEBS triblock copolymer which has a specific gravity of about 0.91, and is said to have a tensile strength of about 3.45 newton/m2 as measured by ASTM method D-412-tensile jaw tester separation speed 25.4 cm/min. The styrene to rubber content of Kraton® G-1650 is said by the manufacturer to be about 29:71, and the Brookfield viscosity is about 8 kg/(m)(sec)(toluene solution, at 25° C., 25% w). The Shore A hardness is about 75.

For making the transparent capsules, preferably a mixture of Kraton® 1650 with Kraton® 1702 is employed, even though Kraton® 1650 is sufficient on its own. The mixture may be preferred in some cases, in order to increase the friability of the capsules, while preserving transparency.

In a second embodiment of the invention, the diblock co-polymer may be employed (having rigid-flexible blocks), even in the absence of a triblock or radial co-polymer. Kraton® 1702 is a diblock co-polymer (styrene-ethylene/propylene). The properties of Kraton® 1702 make it more suitable for use as a viscosity modifier in making the emulsion. According to the second embodiment of the invention, when using Kraton® 1702, in the absence of other copolymers, a hydrophobic solid is added, in order to form capsules. Kraton® 1650, on the other hand, forms a gel, when mixed with oil. When using the mixture of two Kraton polymers, the weight ratio of Kraton® 1650 to Kraton® 1702 is generally from 1:10 to 10:1, more preferably from 3:1 to 7:1, most preferably from 2:1 to 5:1, and optimally from 1:1 to 4:1.

The block co-polymer is employed in the inventive process generally in an amount of from 0.1% to 15%, more preferably from 0.5% to 10%, most preferably from 0.5% to 7%, and optimally from 1% to 4%, by weight of the continuous phase.

In another preferred embodiment, a mixture of oil and wax is employed. In yet another preferred embodiment, a mixture of oil, wax, and the block co-polymer is employed.

Natural or synthetic hydrocarbon oil or mixtures thereof may be employed. Generally, the hydrocarbon oil may be a paraffinic oil, a naphthenic oil, natural mineral oil or the like. Examples include but are not limited to mineral oil, castor oil, vegetable oil, corn oil, peanut oil, jojoba oil, 2-ethylhexyl oxystearate (and other alkyl oxystearates), acetylated lanolin alcohol, alkyl palmitates such as isopropyl palmitate, 2-ethylhexyl palmitate, glycerol triacetates, diosopropyl adipate, dioctyl adipate (and other alkyl adipates), isopropyl myristate, C12 to C15 alcohol benzoates, and the like.

Most preferably, the oil is mineral oil, because it is both economic and most compatible with the block co-polymer.

A preferred ingredient for the continuous phase, in order to strengthen the capsules is a hydrophobic solid. It should be noted, however, that the addition of a hydrophobic solid is not preferred, if transparent capsules are desired. Examples of suitable hydrophobic solids include, but are not limited to wax, microcystalline wax, fatty acid, hydrophobic silica, pigment (e.g., titanium dioxide), fatty alcohols, thermoplastic homo-polymers (preferably, polymers with melting point less than 95° C., to prevent boiling-out of the aqueous phase) such as polyethylene, polypropylene, and mixtures thereof.

Preferably, the hydrophobic solid is selected from paraffin wax, beeswax micro-crystalline wax, polyethylene, polypropylene, most preferably paraffin wax or beeswax, due to their low price and easy processability.

The continuous phase generally includes from 0.1% to 60%, more preferably from 5% to 50%, most preferably from 10% to 40%, and optimally from 30% to 35% of the hydrophobic solid, in order to achieve the best balance between strength of the capsules and their friability in use (% by weight of the total continuous phase).

The continuous phase may include a surfactant as an emulsifier. Sutable surfactants are low HLB surfactants, which may be anionic, cationic, amphoteric, and nonionic, preferably having an HLB of 1 to 10, more preferably from 2 to 7 and most preferably less than 5. In a most preferred embodiment, the surfactant is Neodol® 25-3 available from Shell Chemical Co. The continuous phase generally includes from 0 to 10% of a surfactant, more preferably from 0.1 to 5%, most preferably from 0.3 to 4%, and optimally from 0.5% to 3%, in order to form an emulsion, yet to avoid the formation of a reverse emulsion (% by weight of the total continuous phase).

For simplicity, the material encapsulated within the shell will be referred to as an "enzyme". However, it is within the scope of the present disclosure that materials other than enzymes can be encapsulated by the techniques disclosed herein. These materials include, without limitation, perfumes, vitamins, colorants, anti-oxidants, UV protectors, functional polymers, dye fixatives, anti-wrinkle compounds, color safe and chlorine bleaches, softeners, anti-static agents, deodorant compounds, anti-foam agents, moisturizers, anti-bacterial agents and other useful compounds.

In the first step of the inventive process, an emulsion or dispersion is prepared by mixing the continuous and discontinuous phases, the latter containing the ingredient to be encapsulated, e.g. enzyme solution. The discontinuous phase is selected from the group consisting of an oil, oil solution, an aqueous solution or a solid. In some instances, the discontinuous phase may itself be the desired ingredient and/or colorant. In other instances, the discontinuous phase serves as a vehicle for a benefit agent/colorant. More than one discontinuous phase may be present.

The discontinuous phase is present in an amount of from 0.01 to 45%, more preferably from 5 to 45%, most preferably from 10 to 40%, and optimally from 20 to 35% (% by volume of the capsule) in order to deliver sufficient benefit agent/colorant, provide adequate protection for the benefit agent/colorant and to maintain the ease of processing.

In the case of an enzyme, the discontinuous phase is an aqueous solution of the enzyme. The aqueous enzyme solution may optionally contain a low HLB surfactant, in order to further enhance the formation of the emulsion. If present, the surfactant may be chosen from and employed in the same amounts as the surfactants described above for the continuous phase. The level of the surfactant can be reduced or even eliminated, particularly if suitable agitation is used.

Furthermore, the need for surfactant is entirely eliminated if the shell material is a mixture of thermoplastic polymer with oil, rather than a wax/oil mixture.

If the encapsulated material is an enzyme, the preferred enzymes include proteases, lipases, cellulase, amylase, bleaching enzymes and the like. When selecting enzymes for a liquid detergent system, the most preferred enzymes include proteases and cellulases.

The constituents of the emulsion are preferably present in the following ranges on a weight percent basis: shell material 20% to 90%, most preferably 40% to 60%; surfactant, 0% to 10%, most preferably 0.5% to 3%; water, 0% to 80%, most preferably 25% to 60%; and the encapsulated material (i.e., enzyme), 10% to 80%, most preferably 30% to 60%. Other ingredients can include any additional natural or synthetic oil, preferably mineral oil, plant oil or animal oil (0% to 50%), titanium dioxide (0% to 5%), pigments (0% to 5%), salts (0% to 30%), silica (0% to 5%), colorants (0% to 1%), sugars or sorbitol (0% to 30%) and the like.

In the preferred embodiment, the shell material is melted, then the discontinuous phase is added, with stirring (agitation), to ensure uniform mixing of the ingredients. The resulting emulsion/dispersion is preferably kept at a temperature in the range from 45° C. to 95° C. Most preferably, the use of direct heat is avoided. A most preferred temperature range is from 60° C. to 75° C. (for Kraton®/oil capsules) or 45–65° C. (for wax/oil capsules).

The resulting emulsion/dispersion is directed, either as a stream, or dripping, into the curing solution containing a surfactant agent with a relatively high HLB value and/or a super-wetting, whereby the discrete capsules are formed. Optionally, pressure may be employed in ejecting the stream, in order to ensure that the stream penetrates the surface of the curing solution. The curing solution may also be heated, stirred, and/or pressurized. The curing solution is prepared by combining water and at least one surfactant and/or a super-wetting agent.

The surfactants for the curing solution are selected from the group consisting of high HLB (7 to 25, preferably 10 to 20, most preferably 12 to 16) surfactants, preferably linear and branched nonionic such as Neodol® 25-12, Neodol® 25-9 and Tergitol® 15-S-9. In a most preferred embodiment, the surfactant is Neodol® 25-12, which has a carbon chain length between 12 and 15, with 12 ethylene oxide groups per molecule.

The surface tension modifying agent or super-wetting agent is a highly efficient, low surface energy surfactant. The term "surface tension modifying agent" or "super-wetting" agent is intended to mean any wetting agent or surfactant having an equilibrium surface tension of 35 or less dynes per centimeter at 0.1% concentration in water and as measured by the DuNouy method, preferably less than 31 dynes per centimeter, with less than 30 dynes per centimeter also being preferred. Examples of super-wetting agents are as follows:

| Superwetting Agent | Supplier | Chemical Description |
|---|---|---|
| Zonyl®FSO | duPont | Fluoro chemical with ethylene glycol |
| Fluorad® | 3M Company | Fluorinated alkyl alkoxylate |
| DC Q2® | Dow Corning | Polyoxy ethylene modified polydimethyl siloxane |
| Tergitol® 15-S | Union Carbide | Mixture of linear secondary alcohols reacted with ethylene-oxide |
| Surfynol® TG | Air Products & Chemicals | 2,4,7,9-teramethyl-5-decyne-4,7-diol |
| Makon® OP-9 | Stepan Chemical | Octyl phenol with 9 moles of ethylene oxide |
| Fluowet® OTN | Hoechst Celanese | Fluoroaliphatic oxyethylate |
| Forafac® 1157N | Atochem | Polyfluoroalkyl betaine |
| Silwet® L-77 | OSI specialities | Polyalkylene oxide modified heptamethyltrisiloxane |

The most preferred super-wetting agent is Silwet® L-77 due to its ready availability and optimum performance.

The constituents in the curing solution are preferably present in the following ranges on a weight percent basis: water, 60% to 99%, most preferably 80% to 95%; surfactant and/or a super-wetting agent, 0.1% to 40%, most preferably 5% to 15%.

In the preferred embodiment, the curing solution comprises both the high HLB surfactant and the super-wetting agent.

The super-wetting agent is preferably added as a pre-diluted solution by dripping along, as close to the capsule formation as possible, so that the super-wetting agent is on the surface of the curing solution.

The preferred curing solution contains a super-wetting agent generally in an amount of from 0.1 to 40%, more preferably from 1 to 20%, most preferably from 2 to 10%, and optimally from 3 to 7% (% by weight of the curing solution).

The curing solution is preferably kept at a temperature in the range from 0° C. to 50° C. A most preferred temperature range is from 10° C. to 30° C.

In one preferred embodiment, the emulsion/dispersion of the shell material and encapsulated ingredient is caused to flow (preferably, under pressure) to form a stream which is directed into the curing solution. The stream breaks up into capsules within the curing solution. The stream can be defined by temperature, velocity, width and distance from the upper surface of the curing solution. The size of the orifice through which the stream is directed and the pressure with which it is ejected will also affect the nature of the stream. In a preferred embodiment, the following operating parameters were found to produce encapsulated particles in the range of 200 $\mu$m to 2500 $\mu$m: emulsion temperature: 54–85° C.; vessel pressure: 0–1.05 kg/cm2, most preferably 0.3–0.6 kg/cm2; nozzle distance from curing solution: 2.5–20 cm, most preferably 17.5 cm; nozzle orifice diameter: 0.0125–0.25 cm; curing solution temperature: 0–50° C.

In an alternative preferred method for forming capsules, the emulsion/dispersion of the shell material and the encapsulated ingredient is delivered to the curing solution by a plurality of nozzles: the emulsion is allowed to drip under the static head or the pressure. The dripping forms encapsulated particles upon contact with the curing solution. The size of the nozzle openings and the height of the liquid in vessel ("static head") containing the emulsion and the distance from the curing solution all play a part in the ultimate size of encapsulated particles.

In yet another alternative method, the emulsion may be injected into the curing solution, optionally under pressure (i.e., via a plurality of nozzles in the bottom of the vessel containing the curing solution).

In each embodiment of the invention, the curing solution is continually agitated during the emulsion addition, in order to distribute the formed capsules and keep the surface in motion.

In each of the above processes, the droplets/capsules advantageously have a density greater than that of the curing solution. As such, the formed capsules fall to the bottom of the receiving vessel and do not interfere with new particles as they contact the surface of curing solution. Preferably, the density of the capsules is at least 1.0, most preferably from 1.01 to 2. Suitable methods for increasing the density include, but are not limited to the addition of solid inorganic material, sugar (e.g., sucrose or sorbitol), or any high density solute to the discontinuous phase of the emulsion. For producing enzyme capsules, enzyme solutions are preferably concentrated, prior to the preparation of the emulsion, so as to increase the density, thereby preventing the capsules from floating on the top of the aqueous solution. Increasing the density of the enzyme capsules would also be beneficial, in order to maximize the total enzyme activity in the encapsulated particles, and to decrease or eliminate impurities. Enzyme solutions can be concentrated by exposing an unconcentrated enzyme solution to an aqueous polyol solution, such as 75% sorbitol, wherein the solutions are separated by a membrane. Osmotic pressure causes the concentration of the enzymes in the enzyme solution to increase.

When concentrating the enzyme solution, the enzyme preparation is placed in at least partial contact (e.g., within an enclosure made of a semi-permeable membrane) with a polyol solution, such as sucrose, propylene glycol, glycerol and, more preferably, sorbitol or combinations of polyols. An example of a suitable membrane is Spectra/Por® dialysis tubing (8,000 MWCO (molecular weight cut off)) available from Spectrum, Laguna Hills, Calif. The method allows for various impurities and water to leave the enzyme solution while leaving the enzymes behind and increasing polyol concentration in the enzyme solution. The purification process not only purifies the enzyme solution, thereby enhancing stability, but, if high density material is used such as sorbitol glycerol or sugar, it also concentrates and densifies the enzyme solution. Between 50% to 80% polyol, especially sorbitol, provides a satisfactory rate of transfer, however higher or lower levels can be used depending on desired density of enzyme solution.

Without being bound by theory, it is believed that the outer, hydrophobic surface of capsules attracts the hydrophobic portions of the surfactant molecules in the curing solution, thereby leaving the hydrophilic portions of the surfactant molecules extending from the outer surface of the capsules. Assuming this to be true, the capsules naturally repel each other due to hydrophilic molecule portions extending from the hydrophobic "shell". During processing this is advantageous because the capsules remain separate in solution.

In a final, optional step of the process, in order to make the process continuous, the capsules may be collected out of the curing solution. If the capsules have density higher that that of the curing solution (i.e., higher than the density of water), then the vessel holding the curing solution may have one or more openings in the bottom of the vessel, for the capsules to drain out. The vessel volume may be continuously made up with a fresh curing solution.

If the capsule density is lower than that of water, then the capsules may be collected off the top of the solution by floating the top of the solution off into a collection vessel. Again, the vessel volume may be continuously made up with a fresh curing solution. When this method of collection is employed, it is particularly important that the droplets penetrate the solution surface (e.g., the pressure is employed in forming droplets and/or a super-wetting agent is employed), so that the capsules are formed before the top layer of the curing solution is collected.

The capsules may be directly incorporated into a detergent or personal care composition, or the capsules may be stored in the form of a concentrated stock solution, which generally includes from 10 to 95% of water, more preferably from 20 to 80%, most preferably from 30 to 70%, and optimally from 35 to 60%, in order to attain the best balance between maximum concentration of the capsules and the stock's viscosity, the latter affecting its pumpability (% by weight of the total stock solution).

The following specific examples further illustrate the invention, but the invention is not limited thereto.

Suppliers and chemical description of the ingredients used in the examples are summarized in the following table:

| Trade Name (if appropriate) | Chemical Name | Supplier |
|---|---|---|
| Bowax ® 800 | Petroleum, Hydrocarbon, Microcrystalline Wax | IGI |
| Kraton ® 1650 | Styrene-(ethylene-Butylene)-Styrene tri-block co-polymer | Shell |
| Kraton ® 1702 | Styrene-(Ethylene-Propylene) di-block co-polymer | Shell |
| Sorbitol | D-Glucitol | SPI Polyols |
| Neodol ® 25-3 | Nonionic surfactant: Alcohol Ethoxylate, C12–C15 3 Ethylene oxide groups HLB = 7.8 | Shell |
| Neodol ® 25-9 | Nonionic surfactant: Alcohol Ethoxylate, C12–C15 9 Ethylene oxide groups HLB = 13.1 | Shell |
| Neodol ® 25-12 | Nonionic surfactant: Alcohol Ethoxylate, C12–C15 9 Ethylene oxide groups HLB = 14.4 | Shell |
| Petrolatum | Hydrocarbons | Penreco |
| Blue Dye | Sandolan Blue E-HRL powder 120 | Sandoz Chemicals |
| | Titanium Oxide | Dupont |
| | Cationic surfactant: Dihydrogenated Tallow Dimethyl Ammonium Chloride | Akzo Nobel |
| Tergitol ® 15 S-9 | Nonionic surfactant: Alkyloxypolyethyleneoxyethanol | Union Carbide |
| Silwet ® L-77 | Polyalkylene oxide modified hertamethyltrisiloxane 84%, and Allyloxypolyethylene glycol methyl ether 16% | OSI Specialties |
| IGI ® 1045 Wax | Petroleum, Hydrocarbon, paraffin Wax | IGI |
| | Vitamin C | Cargill Corn Wet Milling |
| Sodium Bicarbonate | Sodium Hydrogen Carbonate | Fischer Scientific |
| Mineral Oil | Hydrocarbons | Fischer Scientific |
| 1218 ® Wax | Petroleum, Hydrocarbon, paraffin Wax | IGI |
| IGI ® 941 Wax | Petroleum, Hydrocarbon, paraffin Wax | IGI |
| Lipolase ® | Lipase | Novo Nordisk |
| Purafect ® | Protease | Genencor International, Inc |

-continued

| Trade Name (if appropriate) | Chemical Name | Supplier |
|---|---|---|
| Arlacel ® P135 | Peg-30 Dipolyhydroxystearate | ICI |
| Properase ® 1600 L | Protease | Genencor International, Inc |

EXAMPLE 1

This example demonstrates the benefit of using Silwet® L77 in curing bath. One of the problems with encapsulation has been stability especially with regard to enzyme stability. In many examples below, sorbitol has been substituted for enzymes due to their like densities and hydrophilic nature.

| Capsule formulation: | |
|---|---|
| 2% Kraton ®1702 | 35% |
| Bowax ® 800 | 20% |
| 70% Sorbitol aqueous solution | 45% |

2% Kraton® 1702 liquid gel was prepared by mixing 2 parts of Kraton® 1702 a 98 parts of mineral oil and heated to 76.7° C. until the mixture became isotropic. 35 parts of this prepared 2% Kraton® 1702 gel was mixed with 20 parts of Bowax® 800 at 60° C. and followed by mixing in 45 parts of 70% sorbitol aqueous solution to form an emulsion. This emulsion was used to form capsules in two different curing solutions: one (outside the scope of the invention) contained only water; the other (within the scope of the invention) contained 1% Silwet® L77 aqueous solution.

Equipment Used:
Re-circulating encapsulation unit powered by a peristaltic pump. Lightening mixer used to create movement in water bath so capsules don't land on one another.

Results:
1) Sprayed emulsion into bath consisting of plain DI (distilled deionized) water (a process outside the scope of the present invention). Results were capsules that stuck to the side of the bath walls. Also, when capsules came in contact with one another they stuck together into one lump and could not be separated even after shaking.

2) Sprayed emulsion into bath consisting of 1% Silwet® L 77 and 99% DI water (a process within the scope of the present invention). Results were capsules that were discrete in that they didn't stick together when they came in contact with one another.

EXAMPLE 2

An emulsion was prepared by mixing 200 g of petrolatum and the mixture of 99 g of 70 w/w % aqueous sorbitol solution and 1 g of 0.1% blue dye aqueous solution at 60° C. in a 500 ml beaker. A bow-tie shape of ring agitator was used for mixing at 250 rpm. 6 g of Neodol® 25-3 was added to enhance the formation of the emulsion. Separately, a curing bath was prepared by mixing 150 g water and 6 g of Neodol® 25-12. The capsules did not stick to each other, were made by dropping emulsion drop-wise into the curing bath by a pipette. The capsules were round in shape and blue in color with the average size of 3000 μm. No visible dye leakage was observed for 24 hours; therefore, these capsules were stable.

EXAMPLE 3

This example used a cationic surfactant (dihydrogenated tallow dimethyl ammonium chloride) in the process according to the invention, in place of Neodol® 25-3, as an emulsifying agent.

| Capsule composition: | |
| --- | --- |
| Petrolatum | 100 g |
| 99 parts of 70% sorbitol and 1 part of 0.1% blue dye | 80 g |
| dihydrogenated tallow dimethyl ammonium chloride | 9 g |

Dihydrogenated tallow dimethyl ammonium chloride was added to petrolatum at 60° C. Sorbitol was then added slowly to bath, so as not to solidify the other ingredients. After mixing for 45 minutes, the emulsion was added drop-wise into curing solution, the latter described in Example 2. Capsules collected in the bath retained structural integrity. After 24 hours, there was no visible dye leakage.

EXAMPLE 4

This example demonstrates the manipulation of capsule density.

An emulsion was made as follows:

| | |
| --- | --- |
| Petrolatum | 200 g |
| Titanium oxide | 2 g |
| dihydrogenated tallow dimethyl ammonium chloride | 20 g |
| 70% Sorbitol aqueous solution | 140 g |

Petrolatum was heated to 60° C., followed by the addition of titanium oxide for adding white color. Subsequently, the temperature was raised to 65.6° C. After the addition of the cationic surfactant, the temperature dropped. The temperature was raised again to 65.6° C., then sorbitol solution was added. Upon addition of sorbitol, temperature dropped to 46.1° C. Temperature was allowed to climb back to 68.3° C.

After mixing for 45 minutes, the emulsion was added drop-wise into curing solution containing:

| | |
| --- | --- |
| Water | 950 g |
| Tergitol ® 15-S-9 | 50 g |

Capsules made from this emulsion did not sink. Additional 15 g 70% sorbitol was added to the emulsion and re-tested. The capsules still floated. Another additional 25 g of 70% sortitol solution was added, thus bringing the total sorbitol level to 180 g. When capsules were dropped into curing solution, they initially began to sink, followed by rising to the surface, then sank to the bottom and stayed. Additional 20 g of sortitol was added thus bringing the total sorbitol level to 200 g. Capsules of this final emulsion sank to the bottom and never floated to the surface. The quality of the capsules was the same, but the high density capsules were easier to process.

EXAMPLE 5

The Examples above used a pipette to form capsules. This example utilized a dispenser, as an apparatus for making capsules. The dispenser was a metal vessel, attached to a support, with multiple pipette tips attached to the bottom. The vessel was also heat-traced and temperature controlled. An agitator was used to maintain a good emulsion inside the vessel. Beneath the vessel was a crystallizing dish; holding a curing solution, on a stirring plate with a stirring bar.

| Capsule formulation | |
| --- | --- |
| Petrolatum | 220 g |
| dihydrogenated tallow dimethyl ammonium chloride | 20 g |
| 99 parts of 70% sorbitol and 1 part of 0.1% blue dye | 220 g |
| Curing solution | |
| Water | 950 g |
| Tergitol ® 15-S-9 | 50 g |

The emulsion was first prepared in a beaker. Petrolatum was added and heated to 65.6° C., followed by the addition of cationic and allowed to fully melt. Sorbitol was then added slowly so as not to reduce bath temperature. The emulsion was subjected to constant mixing and heating. The curing solution was prepared and added to the crystallizing dish and kept at slow agitation. The dispenser's pipette tips were adjusted to approximately 5.1 cm from the surface of curing bath. After the dispenser was preheated, the emulsion was poured into it. Droplets were formed at a near constant rate from the pipette tips. Capsules sank to the bottom and remained spherical. With the naked eye, the capsules appeared to be within a very tight size distribution. The average capsule size was about 2800 to 3000 $\mu$m and the yield was about 110 capsules per tip per minute.

EXAMPLE 6

White capsules were prepared by using the dispenser described in Example 5. The formulation was as follows:

| Capsule formulation | |
| --- | --- |
| Petrolatum | 200 g |
| dihydrogenated tallow dimethyl ammonium chloride | 10 g |
| Titanium oxide | 2 g |
| 99 parts of 70% sorbitol and 1 part of 0.1% blue dye | 192 g |
| Neodol ® 25-3 | 7 g |
| Curing solution | |
| Water | 950 g |
| Neodol ® 25-9 | 50 g |

The emulsion was prepared by adding petrolatum, cationic surfactant and titanium oxide to a beaker and heating to 65.6° C. Sorbitol and Neodol® 25-3 were slowly added. Capsules were then formed following the procedure described in Example 5. The capsules were collected at the bottom of curing bath dish and left there, closely packed. After 24 hours, capsules were examined: with slight agitation, capsules were separated into discrete capsules again. After agitation was stopped, all capsules sank to the bottom again. This indicates that these capsules were stable, because the capsules would float if there were any leakage (since the density of sorbitol is higher than that of water).

EXAMPLE 7

It was noticed that short distance between tips and curing bath resulted in some capsules floating at the surface of curing bath. Capsules may take 3 to 30 seconds to penetrate the surface before sinking to the bottom. A possible explanation may be the high surface tension of the curing bath; the drops falling from a short distance may not be able to penetrate the curing solution surface

| Capsule formulation | |
|---|---|
| Petrolatum | 200 g |
| dihydrogenated tallow dimethyl ammonium chloride | 8 g |
| Titanium oxide | 2 g |
| 99 parts of 70% sorbitol and 1 part of 0.1% blue dye | 184 g |
| Neodol ® 25-3 | 7 g |
| Curing solution | |
| Water | 950 g |
| Tergitol ® 15-S-9 | 50 g |

The preparation followed the procedure described in Example 5. The pipette tips were set to 2.5 cm above the bath surface. Some capsules remained at the surface. After adding 5 droplets of Silwet® L77, the capsules all sank to the bottom.

Thus, it is preferable to employ a combination of a high HLB surfactant and a super-wetting agent in the curing solution, and to increase the kinetic energy of the droplets/stream, so that the droplets/stream can penetrate the surface of the curing solution and the capsules can be enveloped by a surfactant.

EXAMPLE 8

Wax was added in this example to improve the strength of capsules.

| Capsule formulation | |
|---|---|
| Petrolatum | 220 g |
| IGI ® 1045 wax | 80 g |
| 99 parts of 70% sorbitol and 1 part of 0.1% blue dye | 675 g |
| Arlacel ® P135 | 15 g |
| Neodol ® 25-3 | 15 g |
| Curing solution | |
| Water | 940 g |
| Neodol ® 25-9 | 50 g |
| Silwet ® L77 | 10 g |

The preparation was similar to Example 5. Petrolatum, wax and Arlacel® P135 were added together and heated to 68.3° C., followed by a slow addition of sorbitol/dye solution, while maintaining temperature at 68.3° C. After all the sorbitol had been added and well mixed, Neodol® 25-3 was added and allowed to mix for 45 minutes to ensure that it traveled to the emulsion interface. The temperature was then lowered to 62.8° C. The emulsion was then poured into the dispenser and capsules formed in the curing bath. The average capsule size was about 2500 μm. After 48 hours, the color of curing solution remained the same, indicating that the capsules were stable (no leakage of dye).

EXAMPLE 9

In order to make much smaller capsules, a batch of formulation was prepared following the procedure described in Example 5.

| Capsule formulation | |
|---|---|
| Petrolatum | 220 g |
| IGI 1045 wax | 220 g |
| 99 parts of 70% sorbitol and 1 part of 0.1% blue dye | 600 g |
| Arlacel ®P135 | 10 g |
| Neodol ® 25-3 | 20 g |
| Curing solution | |
| Water | 940 g |
| Neodol ® 25-9 | 50 g |
| Silwet ® L77 | 10 g |

Apparatus used for forming droplets was a heat traced recycling loop with a gear pump, a nozzle and a back-pressure valve. The nozzle used in this example was a zero degree straight stream nozzle. The gear pump and the back-pressure valve were used to control the flow rate and kinetic energy of the discharged stream. The stream broke apart upon hitting the surface of curing bath and formed capsules beneath the bath surface. The flow rate was controlled between 0.5 to 1.2 liter/minute. The entire flow rate range supplied sufficient kinetic energy to break the stream into small capsules upon hitting the bath surface. The capsule size distribution was narrow between 300 to 600 microns. This example illustrates that capsule size may be controlled by controlling the kinetic energy of the discharged steam/droplets of the emulsion.

EXAMPLE 10

Vitamin C is a beneficial agent commonly used in personal care products. It is a strong anti-oxidant, therefore, it can be easily be destroyed in a formulation without protection. Thus, it is a good candidate for encapsulation protection. The formulation was as follows:

| Capsule formulation | |
|---|---|
| Petrolatum | 133 g |
| IGI ® 941 wax | 239 g |
| 50 w/w % Vitamin C aqueous slurry | 611 g |
| Silwet ® L77 | 1 g |
| Arlacel ® P135 | 13 g |
| Neodol ® 25-3 | 4 g |
| Curing solution | |
| Water | 940 g |
| Neodol ® 25-9 | 50 g |
| Silwet ® L77 | 10 g |

Wax and Arlacel® were combined and heated to 65.6° C. 50 w/w % Vitamin C slurry was prepared by partially dissolving Vitamin C in water, followed by the addition of Silwett® L77 to help wet the Vitamin C undissolved particles. Since the premix was a slurry, constant agitation was required. When wax and Arlacel® reached 71.1° C., Vitamin C slurry was slowly added and agitated for 5 minutes. Neodol® 25-3 then was added and mixed for another 10 minutes, followed by adding petrolatum. Agitation was continued for additional 20 minutes. Once the system had reached 65.6° C., spraying commenced. Because these capsules were lighter than water, they floated to the top. Thus, the curing solution was filled up to the rim of collection beaker. As capsules were formed, the bath overflowed and carried the formed capsules to the second collection beaker. The overflow allowed for a new surface for collecting capsules. A make-up curing solution was constantly added to the bath to assist the overflow. The height between nozzle tip and curing bath was set in the range of 5 to 15 cm and the flow rate ranged from 0.95 to 1.5 liter/minute. The average capsule size was about 2500 μm.

EXAMPLE 11

Sodium bicarbonate is well know to activate peracid in oral application, however, these components has to be separated in two compartments, which is a very expensive option. This Example demonstrates the utilization of encapsulation to protect sodium bicarbonate from peracid, therefore, the partition for two compartments may be eliminated. The formulation was as following:

| Capsule formulation | |
| --- | --- |
| Petrolatum | 95 g |
| Sodium bicarbonate | 100 g |
| Arlacel ® P135 | 3 g |
| Neodol ® 25-3 | 2 g |
| Curing solution | |
| Water | 940 g |
| Neodol ® 25-9 | 50 g |
| Silwet ® L77 | 10 g |

Petrolatum, Arlacel® and Neodol® were mixed and heated to 65.6° C.; followed by a slow addition of sodium bicarbonate particles. The resulting mixture was allowed to mix for 1 hour. The pH value was measured before the production of capsules. The process described in Example 5 was used for this example. The capsules' size was between 1000 to 2000 μm. After 16 hours, only minor pH increase in the bath was observed and no further change in pH for the next 8 hours. The stable pH was the proof that the capsules were stable.

EXAMPLE 12

One of the problems with encapsulation has been stability especially with regard to enzyme stability. The main reason for activity loss in the past has been processing temperatures that exceeded levels that are suitable for enzymes to maintain activity. In the past, heating was applied directly by means of a hot plate.

A method supplying indirect heat was sought. An encapsulation unit was built from stainless steel jacketed beaker. Nozzles were attached at the bottom of jacketed beaker, through which emulsion was sprayed to form encapsulates. At the top of unit openings were made for pressurized air, a mixing shaft, and a pressure release valve. Hoses were attached to upper and lower portions of beaker, through which water from a temperature controlled water bath flowed. This apparatus allowed for consistent indirect heat supply.

Capsule Formulation was Prepared as Follows:

Kraton®, which is a powdery substance, was converted to gel by mixing with mineral oil at 76.7° C. Wax was then added and a homogeneous isotropic liquid (continuous phase) was formed at 62.8° C. The emulsion was then prepared by emulsifying aqueous solution of sorbitol in the continuous phase. The resulting emulsion was a very stable emulsion, even though an emulsifier was absent: it did not phase separate, for 24 hours at 60° C. Capsules were produced using the re-circulating encapsulation unit described in the previous paragraph.

| Capsule formulation | |
| --- | --- |
| Hydrophobic continuous phase | |
| Mineral oil | 43.83% |
| 1218 wax | 9.00% |
| Kraton ® 1650 | 0.37% |
| Hydrophilic discontinuous phase | |
| 70% Sorbitol solution | 46.80% |
| Curing solution | |
| Water | 4000 g |
| Neodol ® 25-9 | 20 g |
| Silwet ® L-77 | 20 g |

The result was discrete, stable, round-shaped capsules, with an average size of about 1500 μm, which did not stick together when they came in contact with one another.

EXAMPLE 13

Capsules with the following composition were manufactured:

TABLE 2

| Capsule Material Ingredient | Supplier | Weight |
| --- | --- | --- |
| Bowax ®845 | IGI | 660 g |
| Mineral Oil | Penreco | 440 g |
| Concentrated Enzyme* | Genencor | 500 g |
| Sorbitol (70% Solution) | ISP | 400 g |
| Neodol ® 25-3 | Shell | 40 g |

*concentrtrated in-house (see Example 14)

Wax and mineral oil were combined and heated to 65.6° C. While mixing, Neodol® 25-3 was added to the system. In a separate vessel, sorbitol and a concentrated enzyme solution were combined and well mixed. This mixture was slowly added to the wax and oil under constant agitation. After all sorbitol/enzyme mixture was added, the system was mixed for an additional 20 minutes to ensure that the internal, discontinuous phase (sorbitol and enzyme) were well emulsified.

The emulsion was kept in a feeding tank at a temperature of ~65.6° C. Agitation in this vessel was performed with an overhead Gifford Wood homogenizer. Once the emulsion was well agitated, a valve at the bottom of the tank was opened and the pump was turned on. The emulsion was recycled through lines so that the system temperature reached ~65.6° C. to prevent hardening of the wax. After about 5 minutes, a valve to the nozzle assembly was opened. While most of the emulsion continued through the system, about 5% of the flow was diverted for capsule formation. These capsules were formed and collected in a bath of the following concentration; 92% water, 7.5% Neodol® 25-9 (HLB 13.1) and 0.5% Silwet® L-77 (super-wetting agent from OSI Specialties, Greenwich Conn.). These capsules were then removed from the bath and sent for analysis. Enzyme activity was analyzed to yield a 68% recovery. Enzymes were then dosed into a liquid detergent with pH=12.2. After 3 days in this detergent, 83% enzyme activity remained. A sample of non-encapsulated liquid enzyme in the same type of detergent yielded less than 10% activity remaining after 3 days.

EXAMPLE 14

The following examples (Tables 14A and 14B) provided concentrated, densified and purified enzymes by removing various impurities from the enzyme preparation.

Enzyme activity of protease and lipase was measured with a standard enzyme using casein and p-nitrophenylvalerate, respectively as a substrate.

1. About 450 g of enzyme preparation was placed into Spectra/Por® tubing (8,000 molecular weight cut-off regenerated cellulose).
2. The tubing was placed in a beaker containing 3,500 g of 70% sorbitol solution and mixed at room temperature.
3. After about 24 hours the tubing was removed. Density and activity were measured.

Continued operation would result in increased density and activity. Also, the sorbitol solution can be replenished to facilitate the process.

Other Preferred Operating Parameters are as Follows:

pH: about 5 to about 10;

temperature: any temperature that will not harm enzyme activity or stability and that will not cause difficulty of stirring solutions due to high viscosity;

contact time: a couple of hours to days depending on desired density, activity and impurity level; and stirring: recommended to facilitate diffusion.

TABLE 14

A

| Enzyme Preparation | Before Processing | | After Processing | |
|---|---|---|---|---|
| | Activity GU/mg | Density g/ml | Activity GU/g | Density g/ml |
| Protease | | | | |
| Purafect ® | 3,680 | 1.08 | 9,326 | 1.21 |
| Properase ® | 4,200 | 1.08 | 10,200 | 1.22 |
| Lipase | | | | |
| Lipolase ® | 107 | 1.02 | 443 | 1.24 |

B

| Enzyme Preparation | Before Dialysis (Glycerol) | | After Dialysis (Glycerol) | |
|---|---|---|---|---|
| | Activity GU/mg | Density g/ml | Activity GU/g | Density g/ml |
| Properase ® 1600L | 4,300 | 1.05 | 7,840 | 1.20 |

As can be seen in Table 14A, activity levels/density levels increased 2.5/1.12 fold (Purafect®), 2.4/1.13 fold (Properase®) and 4.1/1.22 fold (Lipolase®). As such, activity levels at least doubled and density levels increased by at least about 10%.

Although the illustrative embodiments of the present disclosure have been described herein with reference to the accompanying drawings, it is to be understood that the invention is not limited to those precise embodiments and that various other changes and modifications may be affected therein by one skilled in the art without departing from the scope and spirit of the disclosure.

What is claimed is:

1. A process of making a capsule for detergent or personal care composition, the capsule comprising a discontinuous phase surrounded by a continuous phase, the process comprising the steps of:

(a) preparing an emulsion or a dispersion comprising:
(a1) a hydrophobic material for forming the continuous phase of the capsule;
(a2) from about 0.01% to about 45%, by volume of the capsule, of a discontinuous phase comprising a benefit agent and/or a colorant;

(b) forming droplets of the emulsion or the dispersion;

(c) forming discrete capsules by immersing the droplets into a curing solution comprising from about 0.1% to about 40%, by weight of the curing solution, of a surfactant having an HLB greater than 7.

2. A process of making a capsule for detergent or personal care composition, the capsule comprising a discontinuous phase surrounded by a continuous phase, the process comprising the steps of:

(a) preparing an emulsion or a dispersion comprising:
(a1) a hydrophobic material for forming the continuous phase of the capsule;
(a2) from about 0.01% to about 45%, by volume of the capsule, of a discontinuous phase comprising a benefit agent and/or a colorant;

(b) forming droplets of the emulsion or the dispersion;

(c) forming discrete capsules by immersing the droplets into a curing solution comprising from about 0.1% to about 40%, by weight of the curing solution, of a super-wetting agent.

3. The process of claim 1 wherein the solution in step (c) further comprises from about 0.1 to about 10%, by weight of the curing solution, of a super-wetting agent.

4. The process of claim 1 wherein the discontinuous phase in step (b) is an aqueous solution of an enzyme.

5. The process of claim 4 wherein the enzyme solution further comprises a surfactant.

6. The process of claim 1 wherein the process further comprises the step of increasing the density of the discontinuous phase.

7. The process of claim 6 wherein the discontinuous phase is an aqueous solution of an enzyme.

8. The process of claim 1 wherein step (c) is carried out by dripping the droplets into the curing solution.

9. The process of claim 1 wherein steps (b) (c) are simultaneously carried out by directing the stream of the emulsion or the dispersion into the curing solution.

10. The process of claim 1 wherein step (a) further comprises heating and pressurizing.

11. The process of claim 10 wherein the heating is applied via indirect heat.

12. The process of claim 1 wherein the process further comprises collecting the capsules.

13. The process of claim 1 wherein the process further comprises storing the capsules.

* * * * *